United States Patent
Hopkins et al.

(10) Patent No.: US 7,492,855 B2
(45) Date of Patent: Feb. 17, 2009

(54) SYSTEM AND METHOD FOR DETECTING AN OBJECT

(75) Inventors: Forrest Frank Hopkins, Scotia, NY (US); Peter Michael Edic, Albany, NY (US); Samit Kumar Basu, Niskayuna, NY (US); Bruno De Man, Clifton Park, NY (US); James Walter Leblanc, Niskayuna, NY (US); Xiaoye Wu, Rexford, NY (US); Deborah Joy Walter, Burnt Hills, NY (US); William Robert Ross, Scotia, NY (US); Colin Richard Wilson, Niskayuna, NY (US); Ricardo Scott Avila, Clifton Park, NY (US); Robert August Kaucic, Jr., Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 706 days.

(21) Appl. No.: 10/743,195

(22) Filed: Dec. 22, 2003

(65) Prior Publication Data
US 2005/0031075 A1    Feb. 10, 2005

Related U.S. Application Data

(60) Provisional application No. 60/493,589, filed on Aug. 7, 2003.

(51) Int. Cl.
*G01N 23/04* (2006.01)

(52) U.S. Cl. .......................................... 378/10; 378/57

(58) Field of Classification Search .................. 378/57, 378/10, 5, 9, 12, 122, 4; 382/254–275, 131
See application file for complete search history.

(56) References Cited

U.S. PATENT DOCUMENTS 3,432,664 A    3/1969 Robison (Continued)

FOREIGN PATENT DOCUMENTS

EP    1230950 B1    9/2002

(Continued)

OTHER PUBLICATIONS

"Three-Dimensional Multi-Scale Line Filter for Segmentation and Visualization of Curvilinear Structures in Medical Images," Y. Sato et al., Medical Image Analysis (1998) vol. 2, No. 2, pp. 143-168.

(Continued)

*Primary Examiner*—Hoon Song
(74) *Attorney, Agent, or Firm*—Fletcher Yoder (57) ABSTRACT

A system and method for ascertaining the identity of an object within an enclosed article. The system includes an acquisition subsystem utilizing a stationary radiation source and detector, a reconstruction subsystem, a computer-aided detection (CAD) subsystem, and a 2D/3D visualization subsystem. The detector may be an energy discriminating detector. The acquisition subsystem communicates view data to the reconstruction subsystem, which reconstructs it into image data and communicates it to the CAD subsystem. The CAD subsystem analyzes the image data to ascertain whether it contains any area of interest. Any such area of interest data is sent to the reconstruction subsystem for further reconstruction, using more rigorous algorithms and further analyzed by the CAD subsystem. Other information, such as risk variables or trace chemical detection information may be communicated to the CAD subsystem to be included in its analysis.

70 Claims, 5 Drawing Sheets

U.S. PATENT DOCUMENTS

| | | | |
|---|---|---|---|
| 3,518,433 A | 6/1970 | Owen | |
| 3,714,486 A | 1/1973 | McCrary | |
| 3,783,288 A | 1/1974 | Barbour et al. | |
| 4,200,800 A | 4/1980 | Swift | |
| 4,289,969 A | 9/1981 | Cooperstein et al. | |
| 4,736,396 A * | 4/1988 | Boyd et al. | 378/4 |
| 5,023,895 A * | 6/1991 | McCroskey et al. | 378/4 |
| 5,115,394 A | 5/1992 | Walters | |
| 5,200,626 A | 4/1993 | Schultz et al. | |
| 5,247,561 A | 9/1993 | Kotowski | |
| 5,305,363 A * | 4/1994 | Burke et al. | 378/4 |
| 5,491,734 A | 2/1996 | Boyd et al. | |
| 5,784,481 A | 7/1998 | Hu | |
| 5,838,758 A * | 11/1998 | Krug et al. | 378/53 |
| 5,907,593 A * | 5/1999 | Hsieh et al. | 378/4 |
| 6,115,448 A | 9/2000 | Hoffman | |
| 6,130,929 A * | 10/2000 | Saha | 378/4 |
| 6,207,958 B1 | 3/2001 | Giakos | |
| 6,272,230 B1 * | 8/2001 | Hiraoglu et al. | 382/100 |
| 6,385,292 B1 * | 5/2002 | Dunham et al. | 378/122 |
| 6,418,189 B1 | 7/2002 | Schafer | |
| 6,574,299 B1 | 6/2003 | Katsevich | |
| 6,628,745 B1 * | 9/2003 | Annis et al. | 378/21 |
| 6,721,391 B2 * | 4/2004 | McClelland et al. | 378/57 |
| 7,139,406 B2 * | 11/2006 | McClelland et al. | 382/100 |
| 2002/0085674 A1 | 7/2002 | Price et al. | |
| 2003/0035507 A1 * | 2/2003 | Hsu et al. | 378/4 |
| 2003/0072407 A1 | 4/2003 | Mihara et al. | |
| 2004/0017888 A1 * | 1/2004 | Seppi et al. | 378/57 |
| 2004/0109532 A1 * | 6/2004 | Ford et al. | 378/57 |
| 2004/0213378 A1 * | 10/2004 | Zhou et al. | 378/122 |

FOREIGN PATENT DOCUMENTS

| | | |
|---|---|---|
| EP | 1277439 | 1/2003 |
| GB | 1390575 | 4/1975 |
| WO | 99/67806 | 12/1999 |

OTHER PUBLICATIONS

PCT/US2004/022705, dated Dec. 13, 2005, Int. Filing Date Jul. 15, 2004, International Search Report.

* cited by examiner

SYSTEM AND METHOD FOR DETECTING AN OBJECT

CROSS-REFERENCE TO RELATED APPLICATIONS

This application claims the benefit of U.S. Provisional Application No. 60/493,589, filed Aug. 7, 2003, the entirety of which is incorporated herein by reference.

BACKGROUND

The invention relates generally to the detection of objects located within articles. More particularly, the invention relates to the detection of contraband, objects considered illegal for transport in luggage or mail parcels.

There has always been, and there continues to be, a demand for heightened security surrounding various communication and transportation avenues. For example, metal detectors and x-ray machines are standard security devices employed at airports for screening passengers and their carry-on luggage. The United States Postal Service also employs x-ray technology for screening parcels.

The capability for automatically screening luggage in an efficient and cost-effective manner is currently non-existent. The screening systems currently in place record false positives at higher than desirable rates. The high number of false positives forces alternative follow-on inspections, such as trace detection or manual inspection of the luggage, thereby increasing the average screening time per bag substantially. There remains a need for a high-throughput (e.g., at least one thousand scanned checked bags per hour) automatic screening system for ascertaining whether a piece of luggage or a mail parcel contains an object which may be harmful, such as, for example, an explosive device or material.

SUMMARY

The present invention describes a system and a method for ascertaining whether a harmful object, such as an explosive device or material, is located within a closed article, such as a piece of luggage or a parcel.

One aspect of the invention is a system for detecting an explosive within an article. The system includes an acquisition subsystem including a scanner incorporating stationary radiation sources and detectors and adapted to acquire intensity measurements pertaining to the object, and a reconstruction subsystem, in communication with the acquisition subsystem, for generating view data from the intensity measurements and for reconstructing the view data into image data representative of the object.

Another aspect of the invention is a system for detecting an explosive within an article that includes a transportation means for transporting the article. The system also includes an acquisition subsystem comprising a scanning including stationary radiation sources and detectors and having at least one scanning detector that is adapted to acquire intensity measurements that can be processed into view data pertaining to an object. The system further includes a reconstruction subsystem, comprising a plurality of reconstruction stages, for reconstructing the view data into image data representative of the object, and a computer-aided detection subsystem, comprising a plurality of computer-aided detection stages, for analyzing the image data.

Another aspect of the invention is a system for detecting an explosive within an article that includes an acquisition subsystem for acquiring intensity measurements pertaining to the object. The system also includes a reconstruction subsystem, in communication with the acquisition subsystem, for generating view data from the intensity measurements and for reconstructing the view data into image data, a computer-aided detection subsystem for analyzing the image data, and at least one additional source of information pertaining to the object, wherein the image data and the at least one additional source of information assist in identifying the object.

Another aspect of the invention is a method for detecting an explosive within an article. The method includes the steps of acquiring information pertaining to the object with an acquisition apparatus having a scanner incorporating stationary radiation sources and detectors and reconstructing an image representative of the object based upon the acquired information.

Another aspect of the invention is a method for detecting an explosive within an article. The method includes the steps of acquiring information pertaining to an object located within the article with a scanning device incorporating stationary radiation sources and detectors and having at least one scanning detector and communicating the acquired information to a plurality of reconstruction stages. The method also includes the steps of reconstructing the acquired information into image data with the plurality of reconstruction stages and analyzing the image data to identify whether the object is an explosive device.

Another aspect of the invention is a method for detecting an object and distinguishing between objects based on x-ray energy dependent material properties. The method includes the steps of scanning an article with a computed tomography machine to acquire information pertaining to the object, discriminating between high-energy and low-energy signatures, reconstructing image data representative of the object based upon the high-energy and low-energy signatures, and analyzing the reconstructed image to identify the object.

These and other advantages and features will be more readily understood from the following detailed description of preferred embodiments of the invention that is provided in connection with the accompanying drawings.

DETAILED DESCRIPTION OF PREFERRED EMBODIMENTS

Figure 1:
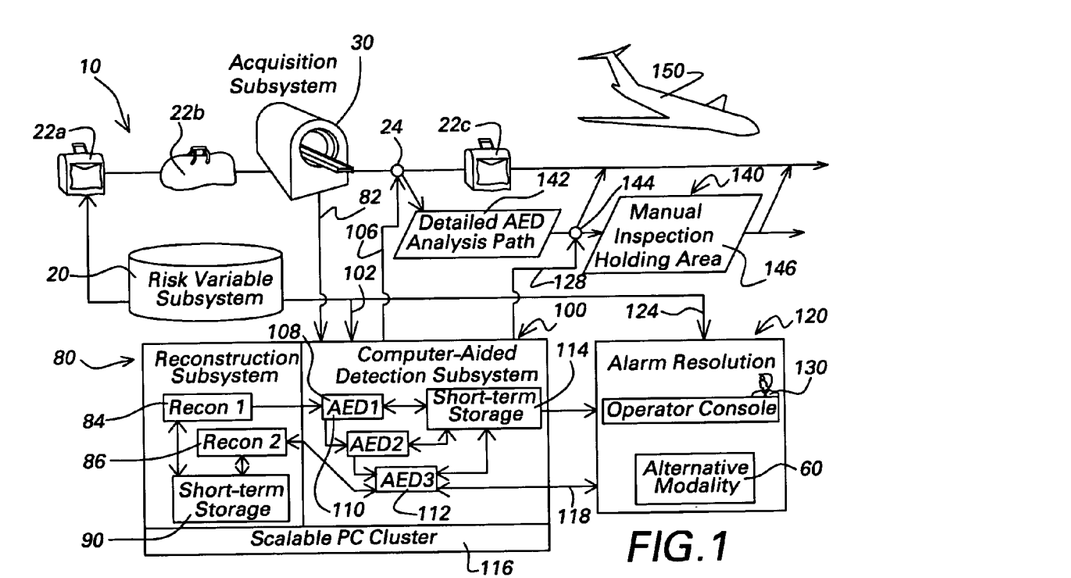
FIG. 1 is a schematic view of an object detecting system in accordance with an exemplary embodiment of the invention.

With reference to FIG. 1, an object detecting system 10 is schematically shown. The object detecting system 10 includes a risk variable subsystem 20, an acquisition subsystem 30, an alternative modality subsystem 60, a reconstruction subsystem 80, a computer-aided detection (CAD) subsystem 100, and an alarm resolution subsystem 120. The object detecting system 10 is adapted to accommodate a high throughput of articles, for example, screening of upwards of one thousand individual pieces of luggage within a one hour time period, with a high detection rate and a tolerable number of false positives.

The risk variable subsystem 20, which is a subsystem that collects externally provided risk data, serves to alter the parameters by which a specific article is investigated. The risk variable subsystem 20 includes a compendium of risk related information appropriate for a specified task. For example, a risk variable subsystem 20 used in a luggage screening operation at an airport may include information for a specific piece of luggage, such as luggage 22a, 22b or 22c (hereinafter referred to as luggage 22n), information related to a threat level index (e.g., red, orange, yellow, etc.), threat information directed at a specific region of the world, country, or airport, information on the destination of the specific luggage, information on the nationality or other relevant profile parameters of a passenger associated with the specific luggage, or information directed to any other appropriate factors. The information in the risk variable subsystem 20 may be used in conjunction with other information gleaned regarding a specific piece of luggage to ascertain whether that luggage includes any object which may be harmful to passengers on an airliner containing that luggage, such as, for example, an explosive device. If certain threat-related information is associated with a specific piece of luggage, the risk variable subsystem 20 may heighten investigative parameters used on that piece of luggage. The information obtained through the risk related subsystem 20 is added to the totality of information utilized by the CAD subsystem 100 through a link 102.

Figure 3:
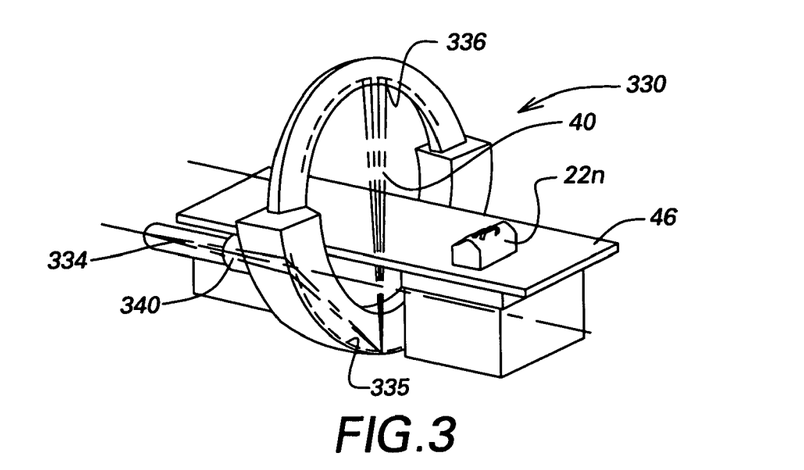
FIG. 3 is a perspective view of an exemplary embodiment of an acquisition subsystem for use in the object detecting system of FIG. 1.

FIG. 3 illustrates an embodiment of the acquisition subsystem 30 for use in the object detection system 10, namely a $5^{th}$ generation computed tomography (CT) scanner 330, a CT scanner having stationary radiation sources and detectors. The acquisition subsystem 330 includes a vacuum housing chamber 334 that generates an electron beam 340. The electron beam 340 is swept by magnetic fields and scans an arc-shaped target 335. Upon being struck by the electron beam 340, which typically scans 210 degrees or so in about 50 ms, the target 335 emits a moving fan-like beam of x-rays 40 that passes through a region of the luggage 22n lying atop the conveyor belt 46, and then registers upon a detector array 336 located diametrically opposite. The detector array 336 measures intensity profiles of transmitted x-ray beams, allowing generation of view data, or projection data, that is then communicated to the reconstruction subsystem 80.

Figure 4A:
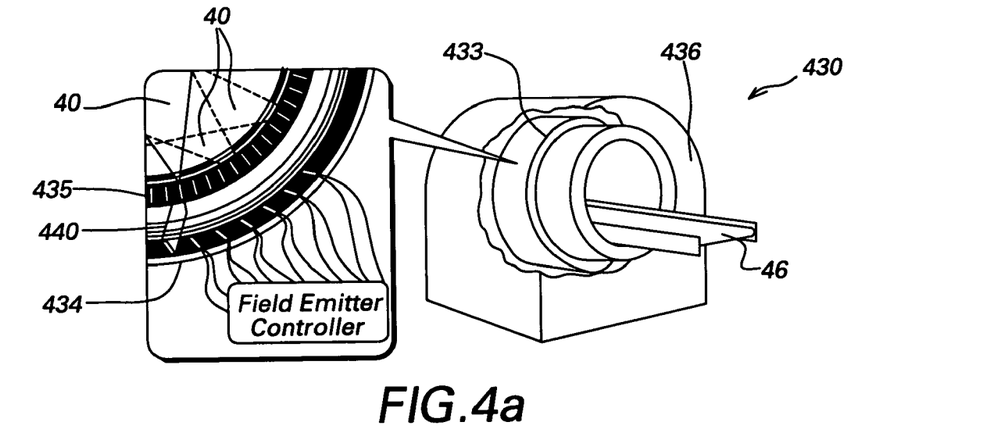
FIGS. 4a and 4b are partial cross-sectional perspective views of another exemplary embodiment of an acquisition subsystem for use in the object detecting system of FIG. 1.
Figure 4B:
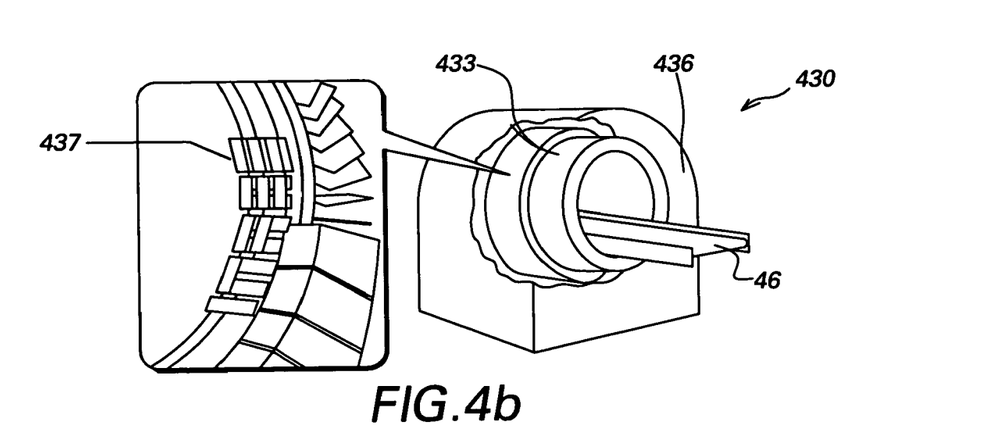

Next, with reference to FIGS. 4a and 4b, another embodiment of the acquisition subsystem 30 for use in the object detection system 10 is described. Like the acquisition subsystem 330 (FIG. 3), the acquisition subsystem 430 includes a CT scanner having stationary radiation sources and detectors. The stationary acquisition subsystem 430 includes a source ring 433 including distributed electron field emission devices 434. The acquisition subsystem 430 further includes a detector ring 436 adjacent to the source ring 433. As illustrated, the detector ring 436 is offset from the source ring 433. It should be appreciated, however, that "adjacent to" should be interpreted in this context to mean the detector ring 436 is offset from, contiguous with, concentric with, coupled with, abutting, or otherwise in approximation with the source ring 433. The detector ring 436 includes a plurality of discrete detector modules 437 which may be in linear, multi-slice, or area detector arrangements. An exemplary embodiment of the detector module 437 includes a detector cell having a pitch of, for example, two millimeters by two millimeters, providing an isotropic resolution on the order of one millimeter in each spatial dimension. Another exemplary embodiment of the detector module includes a detector cell having a pitch of one millimeter by one millimeter. Each of the electron field emission devices 434 sends an electron beam 440 to a target ring 435, which produces a fan-like beam of x-rays 40 toward the luggage 22n (FIG. 3) on the conveyor belt 46. The x-rays 40 travel through the luggage 22n, are attenuated to some extent by the contents of the luggage 22n, and impinge upon one or more discrete detector modules 437. A suitable detector module 437 may include a scintillation element or a direct conversion material. The detector modules 437 form intensity measurements from the x-rays 40, which are then generated into a measured sinogram, or view data 200 (FIG. 5), and the view data is then communicated to the reconstruction subsystem 80.

An advantage of the mostly stationary acquisition systems 330, 430 is that the reduction of moving parts allows for a higher throughput of articles for scanning than the throughput capacity of CT scanners utilizing rotating gantries.

The acquisition subsystems 330, 430 may include an energy discriminating function to allow the use of a multi-energy CT approach. An energy discriminating function utilizes information regarding the attenuation of x-rays of different energies penetrating the object of interest. Typically, this information can be obtained either by acquiring projection data with two or more different source spectral profiles (achieved by varying voltage, source filtration, or a combination of the two) or by achieving a spectral decomposition of a single source spectrum in the detector elements. For example, the acquisition subsystems may include at least one detector for detecting x-rays from at least two different incident x-ray energy spectra. Alternatively, the acquisition subsystems may include either an energy discriminating detector adapted to acquire energy sensitive measurements in the photon counting mode or an energy discriminating detector that includes an assembly of two or more x-ray attenuating materials, the signals from which can be processed in either a photon counting or a charge integration mode.

A conventional CT scanner scans with a source at a particular high voltage, such as, for example, between 120 and 140 keV. Such CT scanners give a broad spectrum of energy data. As an x-ray penetrates an object, attenuation occurs. Attenuation is greater for lower energy signals, which causes beam hardening. Beam hardening complicates the analysis of an object by overestimating its mass, thereby distorting the image produced. A CT scanner capable of dual energy scanning, namely the energy levels of incident x-rays are classified as either high-energy signals or low-energy signals, will allow computation of a pair of data sets. One of the data sets can be directed to mass density, while the other can be directed to an average Z value (atomic number) for items within the article being scanned. The acquisition subsystems 330, 430 may be equipped with a detector that electronically discriminates between high- and low-energy spectra, or multiple energy spectral regimes. The multiple-energy-discriminating detector may be equipped either with a scintillation element or with a direct conversion material. Alternatively, the acquisition subsystems 330, 430 may perform two or more sets of scans for each article, one set of scans at one energy spectrum and the other set of scans at another energy spectrum.

The alternative modality subsystem 60 (FIG. 1) is an optional subsystem for use in the object detection system 10. The alternative modality subsystem 60 may include one or more additional investigative modalities that may be useful in ascertaining the identity of suspicious objects within closed articles. Examples of suitable additional investigative modalities include, for example, a trace detection subsystem, a coherent scattering detection subsystem, and a quadrupole resonance subsystem. The alternative modality subsystem 60 may be incorporated with the acquisition subsystem such that as a piece of luggage 22n passes by the acquisition subsystem, the alternative modality subsystem 60 can obtain additional data pertaining to the object within the luggage 22n. For example, for an alternative modality subsystem 60 having a trace detection subsystem, the trace detection subsystem can obtain data pertaining to average chemical compositions of material found within the luggage 22n. Such a trace detection subsystem may include chemical detectors and an apparatus designed to create a current or puff of air toward the detectors. The puff or current of air will carry minute traces of chemicals from the luggage 22n toward the detectors. Alternatively, such a trace detection subsystem may utilize a swipe methodology at a predetermined location. By swiping the exterior of the luggage 22n, the swipe will pick up minute traces of chemical compositions resident thereon. The swipe then can be analyzed to determine the likely chemicals found within the luggage 22n. The additional information gained through the alternative modality subsystem 60 is added to the information used by the CAD subsystem 100 through a link 118.

Figure 5:
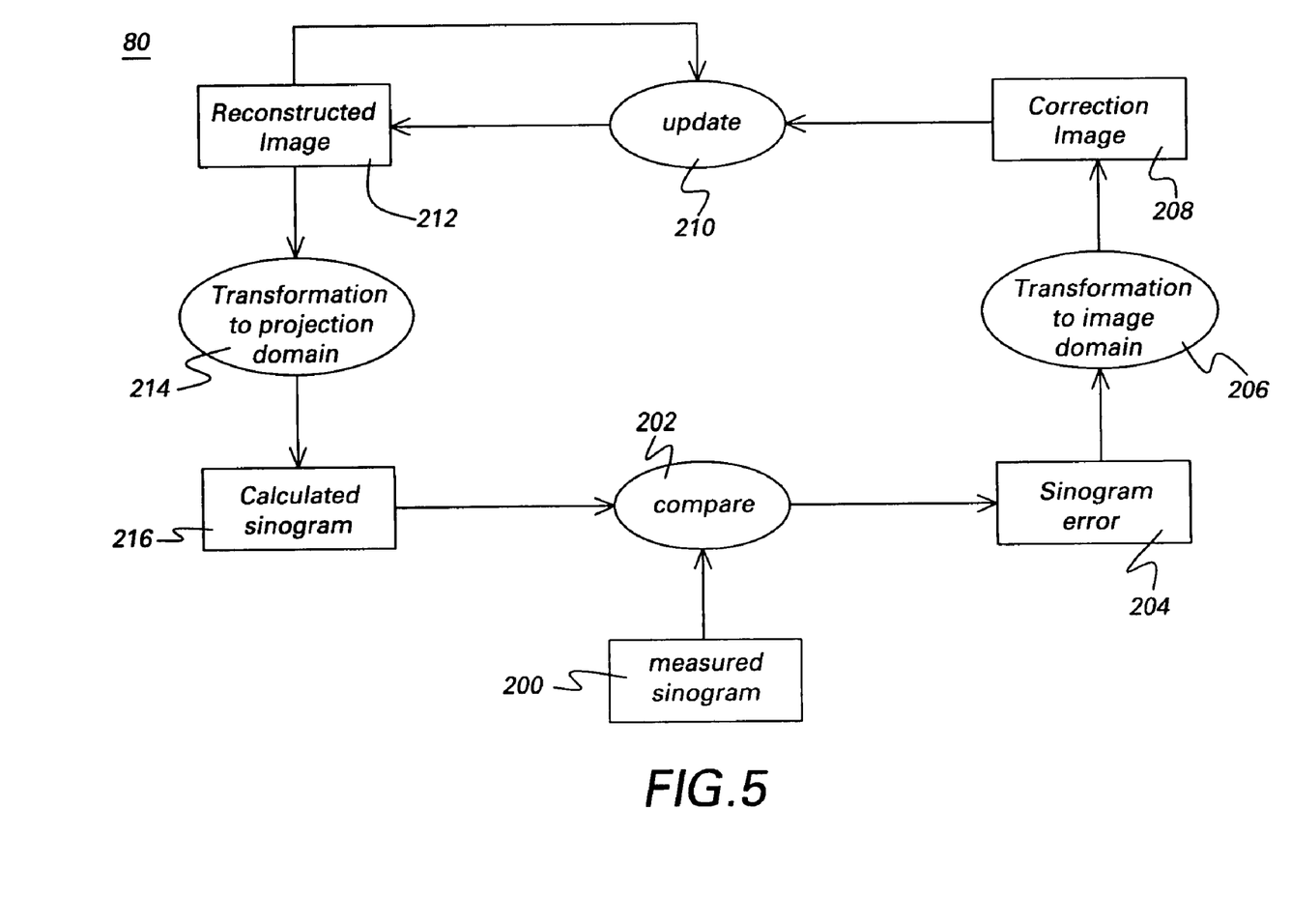
FIG. 5 illustrates an exemplary method for reconstructing image data in accordance with an embodiment of the invention.

The reconstruction subsystem 80 is linked to the acquisition subsystem 30 through a link 82. In the FIG. 1 embodiment, intensity measurements are used to generate view data. The view data, which is obtained from the acquisition subsystem 30, is received by the reconstruction subsystem 80 through the link 82. In an alternate embodiment, the intensity measurements are transferred to the reconstruction subsystem 80, which then generates the view data 200. The reconstruction subsystem 80 includes a plurality of reconstruction stages 84, 86, each of which includes one or more algorithms for reconstructing the view data into image data. Short-term storage 90 is included within the reconstruction subsystem 80 and is in communication with each of the reconstruction stages 84, 86. The reconstruction subsystem 80 functions to reconstruct the view data 200 received from the acquisition subsystem 30 into image data which can then be communicated to the CAD subsystem 100 for further analysis. Although illustrated as including two reconstruction stages 84, 86, it should be appreciated that the reconstruction subsystem 80 may include only one reconstruction stage or three or more reconstruction stages as necessary.

The FIG. 1 CAD subsystem 100 is in connection via link 106 with a node 24 within the transportation line of the luggage 22n. The node 24 is a decision point at which, based upon information obtained through the CAD subsystem 100, one or more pieces of luggage 22n will be shunted out of line to the aircraft 150 and to a manual inspection subsystem 140 including an automated explosives detection analysis area 142 and a manual inspection holding area 146.

The CAD subsystem 100 includes a plurality of automated explosives detection (AED), or CAD, stages 108, 110, 112 in communication with the reconstruction stages 84, 86. As illustrated in FIG. 1, the reconstruction stage 84 is in communication with the AED stage 108, which in turn is in communication with the AED stage 110 and the short-term storage 114. The reconstruction stage 86 is in communication with the AED stage 112, which in turn is in communication with the alternative modality subsystem 60 and the alarm resolution subsystem 120 through the link 118, the short-term storage 114, and the AED stage 110. A scalable cluster of personal computers 116 may be employed by both the reconstruction subsystem 80 and the CAD subsystem 100 to provide sufficient computing speed to the object detecting system 10. The CAD subsystem 100 works in conjunction with the reconstruction subsystem 80 to ascertain whether a specific piece of luggage 22n has an area of interest within the image data. By "area of interest" is meant an area within the image data that has not yet been resolved or reduced into a specific object or into an object that, although not completely identified, has been identified enough to ascertain that it is not harmful.

The CAD subsystem 100 is in connection with the alarm resolution subsystem 120 through link 118. The alarm resolution subsystem 120 includes a plurality of operator consoles 130. Information from the risk variables subsystem 20 is communicated to the alarm resolution subsystem 120 via a link 124. The information from the risk variables subsystem 20, as well as information derived through the alternative modality subsystem 60, are communicated to the AED stage 112 through the link 118. The decision of the CAD subsystem 100 is sent via a link 128 to a decision node 144, at which the specific luggage 22n will either be moved back to the line to the aircraft 150 or will be moved to the manual inspection holding area 146, at which a manual inspection of the specific luggage 22n will be undertaken to resolve the area of interest.

Figure 2:
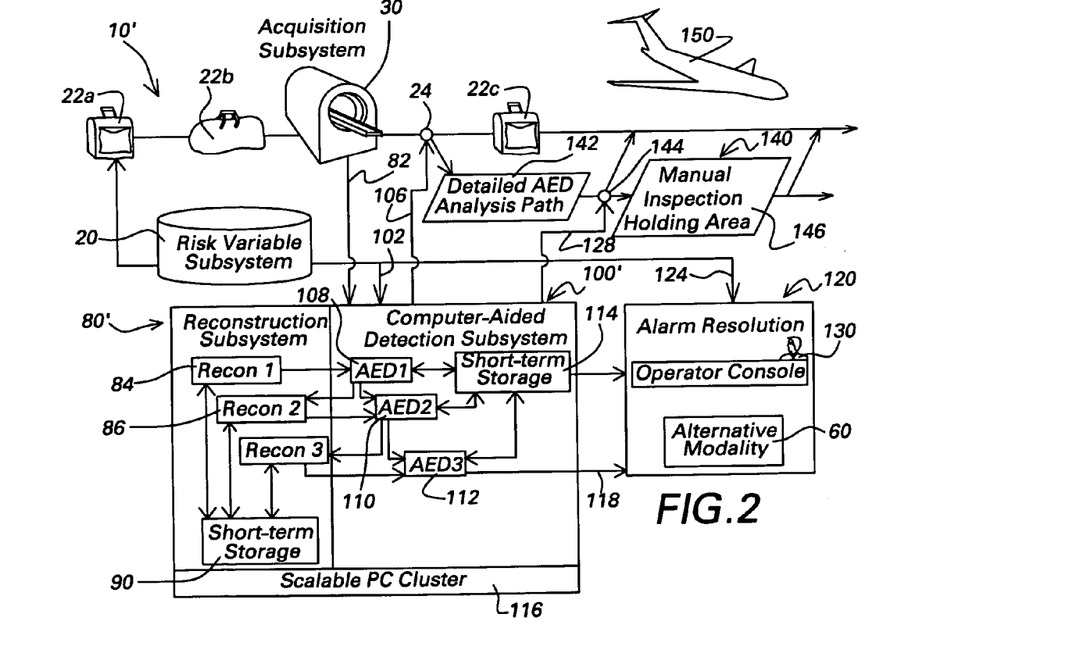
FIG. 2 is a schematic view of an aspect of the object detecting system of FIG. 1.

An aspect of the general object detection system 10 architecture is illustrated in FIG. 2. As shown therein, the object detection system 10' has a similar architecture as the object detection system 10 of FIG. 1. One difference is that the reconstruction subsystem 80' includes three reconstruction stages 84, 86, 88. Another difference is in the pathways between the reconstruction subsystem 80' and the CAD subsystem 100', which will now be described. In the FIG. 2 embodiment, the reconstruction stage 84 is in communication with the AED stage 108, which in turn is in communication with the short-term storage 114, the AED stage 110, and the reconstruction stage 86. The reconstruction stage 86 is in communication with the AED stage 110, which in turn is in communication with the short-term storage 114, the AED stage 112, and the reconstruction stage 88. The AED stage 112 is in communication with the short-term storage 114 and the alarm resolution subsystem 120 containing the alternative modality subsystem 60 through the link 118. It should be appreciated that the illustrated architectures of the object detection subsystems 10, 10' are only indicative of the type of arrangement contemplated by the invention, and should not be seen to be exhaustive.

Next will be described a method for reconstructing image data using filtered back-projection. Filtered back-projection is a set of mathematical formulae that eliminate the necessity of performing iterative manipulations of the image data. Beginning with the view data, numerous pre-processing steps that are mathematically prescribed are performed to create modified view data. Then, a back-projection is performed to reconstruct the view data into the image domain to obtain one or more cross-sectional images of the object scanned. An example of mathematical formulae that are sufficient for a three-dimensional filtered back-projection may be found in U.S. Pat. No. 6,574,299, the entire contents of which is incorporated by reference herein.

Next will be described, with reference to FIGS. 1 and 5, a method for determining the presence of an object within an article. This method is an example of one of many methodologies for reconstruction, as is known to those skilled in the art. Reconstruction may be done wholly in software, wholly in hardware, or in some combination of both software and hardware.

For sake of simplicity, the example will be directed to the detection of an explosive device or material within a piece of luggage 22n. As the luggage 22n is transported through the acquisition subsystem 30, a plurality of data packets of intensity measurements, which can be processed to produce a measured sinogram, are prepared by the acquisition subsystem 30. As the luggage 22n continues on to the decision node 24, the measured sinogram, or view data, is communicated via link 82 to the reconstruction subsystem 80. In an alternate embodiment, the reconstruction subsystem 80 receives the intensity measurements from the acquisition subsystem 30 and computes the view data. The reconstruction subsystem 80 processes the view data and generates images of the luggage 22n. One of several reconstruction algorithms may be useful for this purpose: filtered back-projection techniques, Radon-transform inversion techniques, iterative reconstruction, statistical reconstruction, or other multi-pass reconstruction techniques. Independent of the reconstruction technique, the resultant image quality in reconstructions of the luggage 22n must be sufficient to meet the detection criterion of the CAD subsystem 100. For example, a preferred algorithm used to create the reconstructed image 212 may be capable of reconstructing the object with a voxel size commensurate with the size of the features that are the focus of the detection. Preferably, the algorithm used to create the reconstructed image 212 may be capable of reconstructing the object with an isotropic voxel size of two millimeters (two millimeters in each spatial dimension). A more preferred algorithm may be capable of reconstructing the object with an isotropic voxel size of one millimeter in each spatial dimension. At that point, the reconstructed image 212 is communicated to both the short-term storage 90 and the AED stage 108 within the CAD subsystem 100. Although the voxel is described as having isotropic dimensions, the size of the voxel in each spatial dimension may be chosen separately to meet a specific imaging requirement.

The AED stage 108 performs an analysis of the image data of the reconstructed image 212 to ascertain whether there is an area of interest within that image data. The AED stage 108 may be programmed to utilize an algorithm that searches for a specific characteristic feature, such as, for example, mass, density, composition, surface area, surface area to volume ratio, edge characteristics, or shape. If an area of interest is found within the image data, for example a suspicious object is ascertained to be within the image data, the data representing the area of interest is communicated to both the short-term storage 114 and the AED stage 110. Further analysis of the data representing the area of interest may be performed in the AED stage 110, which communicates this analysis to both the short-term storage 114 and the AED stage 112.

The AED stage 112 communicates this analysis to the reconstruction stage 86, which performs the same reconstruction methodology as described above, or an alternate technique may be employed to improve image quality in the reconstructed images. The reconstruction stage 86 will be programmed with an algorithm designed to improve the image (sharpen, enhance, reduce noise, etc.) of the area of interest. For example, the reconstruction stage 86 may include an algorithm that is capable of reconstructing the area of interest, i.e., the object, with an isotropic voxel size of one millimeter or less in each spatial dimension. Such an algorithm will, of necessity, entail more computational time than the algorithm of the reconstruction stage 84.

Once the stop criterion has been met, i.e., an isotropic voxel size of one millimeter or less in each spatial dimension has been achieved by the reconstruction stage 86, the data representing the reconstructed image 212 of the area of interest is communicated to the short-term storage 90 and to the AED stage 112, at which further analysis of the area of interest may be performed. The AED stage 112 may perform further analysis of the area of interest, comparing one or more features of the object with various exemplary objects. The algorithm utilized by the reconstruction stages 84, 86 may be effective at reducing artifacts in the image data generally caused by metallic objects. Alternatively, the reconstruction stages 84, 86 may include an algorithm effective at varying the voxel size in the image data, or effective at compensating for noise in the image data, or directed at iteratively and statistically reconstructing the image data. As another alternative, the reconstruction stages 84, 86 may include an algorithm effective at varying the parameters for material decomposition to optimize detection of an explosive material. After subjecting the data representing the area of interest image data to the AED stage 112, the reconstructed image 212 of the area of interest is communicated to the short-term storage 114 and the alarm resolution subsystem 120. Further, a signal is sent from the CAD subsystem 100 via the link 128 to the decision node 144 to pull a specific piece of luggage 22n out of line to the aircraft 150 and into the alarm resolution area 142 if the area of interest has not been resolved sufficiently to ascertain that the object is not harmful.

The area of interest image data 212 is communicated to the alarm resolution subsystem 120 via the link 118. The operators manning the operator consoles 130 can review the reconstructed image 212 of the area of interest, as well as the image data stored in the short-term storage 114 and any other information, such as material composition, etc. If the operators are able to resolve the area of interest to be an object that is not harmful, the operators can release the specific piece of luggage 22n back to the aircraft 150. If the operators cannot resolve the area of interest sufficiently, they can send the specific piece of luggage 22n to the manual inspection holding area 146 for a manual search.

Alternatively, and with reference to FIGS. 2 and 5, the AED stage 108 may perform an analysis of the image data of the reconstructed image 212 to ascertain whether there is an area of interest within that image data. The results of that analysis are communicated to the short-term storage 114, the AED stage 110, and the reconstruction stage 86. The reconstruction stage 86 will be programmed with an algorithm designed to improve the image (sharpen, enhance, reduce noise, etc.) of the area of interest. Data representing the improved image of the area of interest is then communicated from the reconstruction stage 86 to the AED stage 110 for further analysis. The further analyzed data representing the improved image of the area of interest is then communicated to the short-term storage 114, the AED stage 112, and the reconstruction stage 88. The reconstruction stage 88 performs yet more reconstruction of the area of interest data, and communicates that reconstruction to the AED stage 112, which in turn communicates it to the short-term storage 114 and the alarm resolution subsystem 120 and the alternative modality subsystem 60 through the link 118.

Acquisition apparatus using detectors having stationary radiation sources and detectors, such as the acquisition subsystem 430 (FIGS. 4a, 4b), will provide intensity/view data with gaps in the data. The gaps are a byproduct of the lack of a moving source and a moving detector array. Exact algorithms, such as the algorithms described in U.S. Pat. No. 6,574,299, generate images with reduced image quality if there is mathematically incomplete view data, i.e., view data with gaps. Hence, for an object detection system that utilizes an acquisition apparatus with detectors having stationary radiation sources and detectors and a reconstruction subsystem using exact algorithms, some form of correction is required of the view data to improve image quality. For example, a pre-correction may be performed, namely interpolation techniques can be used to fill in the gaps in the view data. The pre-correction may be followed up with a post-correction, which may be an iterative reconstruction process after using the exact algorithms. While exact algorithms operating on mathematically complete view data in most instances will provide enhanced quality in the image data, for examining luggage to ascertain the presence of a harmful object, approximate algorithms may be sufficient.

Figure 6:
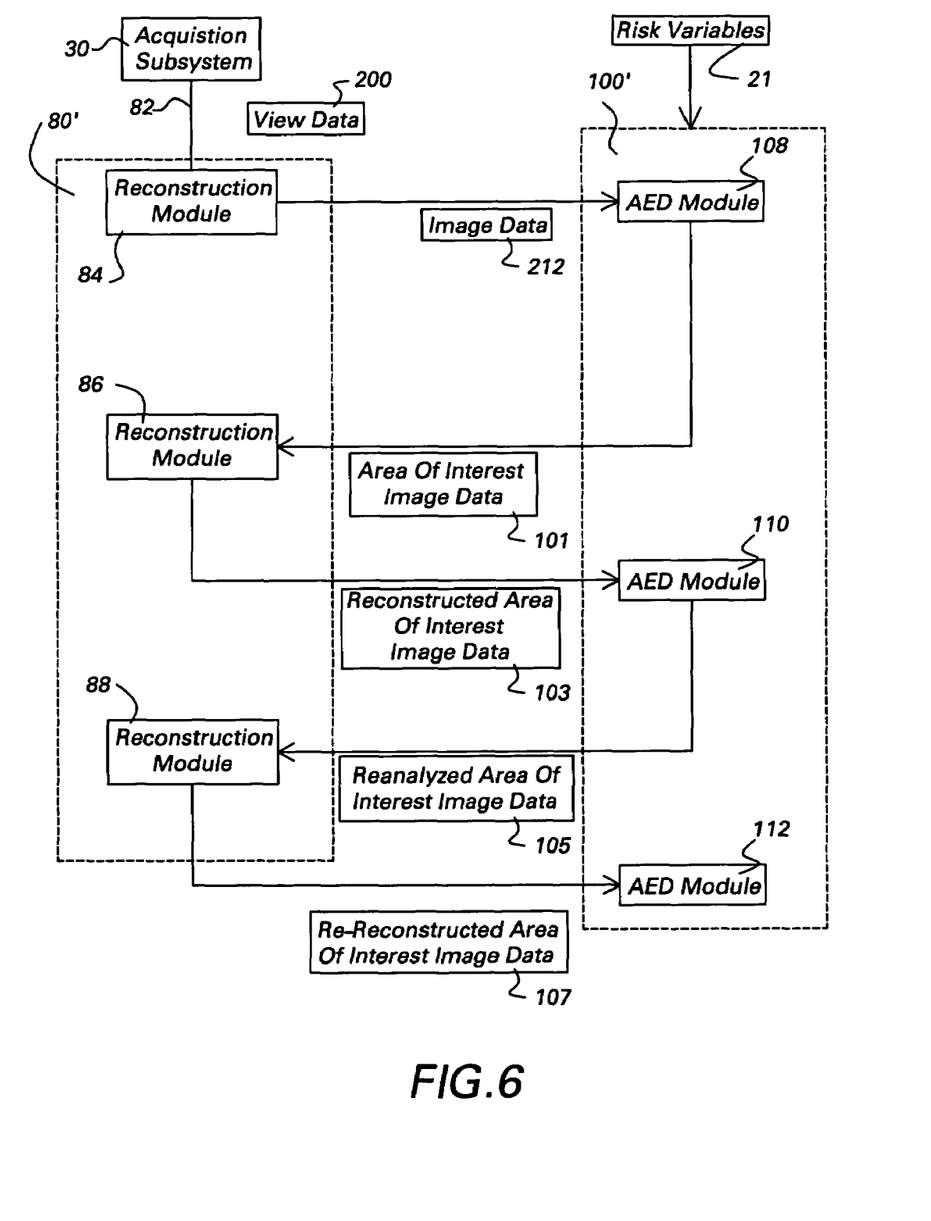
FIG. 6 is a block diagram illustrating an exemplary process for detecting an object within an article.
Figure 7:
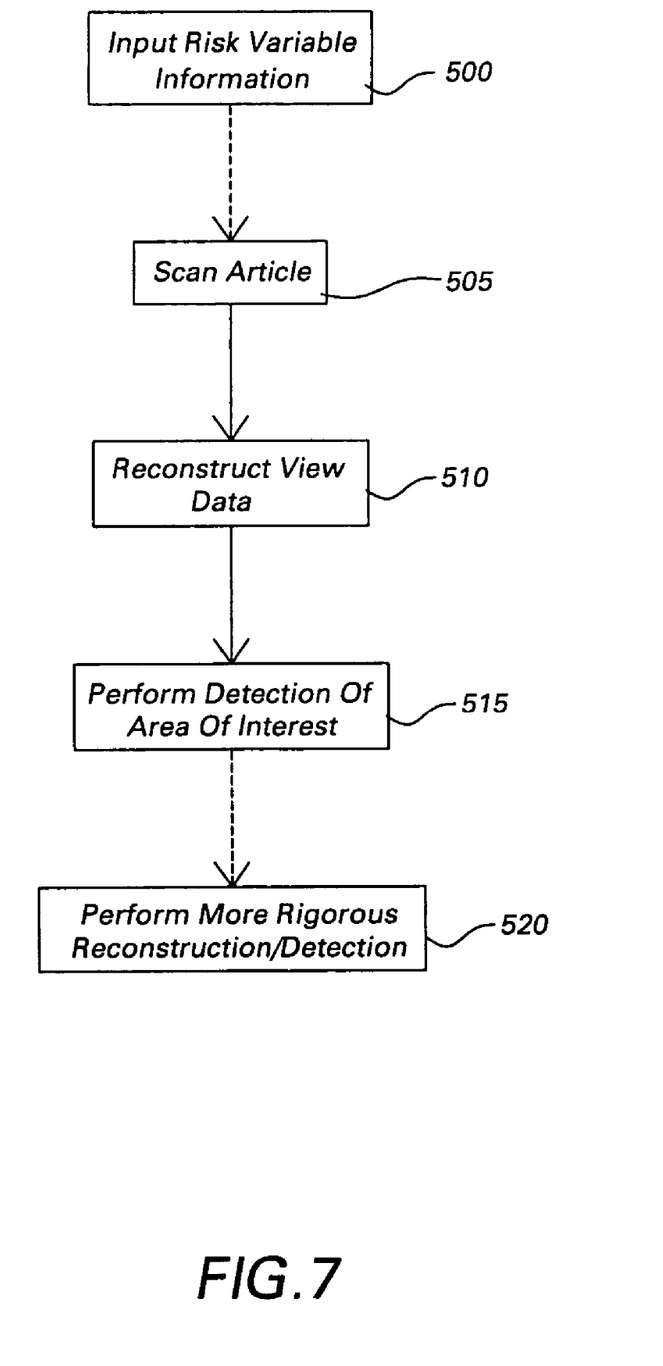
FIG. 7 illustrates exemplary process steps for the process of FIG. 6.

With specific reference to FIGS. 6 and 7, next will be described an exemplary process for detecting an object located within an enclosed article, such as, for example, luggage 22n. Each piece of luggage 22n has associated with it certain risk variables. At a risk variable subsystem 20 (FIG. 2), the applicable risk variable information 21 is associated with the piece of luggage 22n at Step 500 (FIG. 7). These risk variables 21 are communicated to the CAD subsystem 100'. The luggage 22n is then scanned by the acquisition subsystem 30 at Step 505. It should be appreciated that other acquisition subsystems may be utilized, such as, for example, acquisition subsystem 330 (FIG. 3) or 430 (FIG. 4a, 4b).

The acquisition subsystem 30 obtains intensity measurements, which are then formulated into view data, or projection data, 200 from the scan of the luggage 22n. The view data 200 is communicated to the reconstruction subsystem 80, namely the reconstruction stage 84, via link 82 (FIG. 6). The reconstruction stage 84 reconstructs the view data 200 into image data 212 at Step 510. For example, the reconstruction stage 84 may utilize an algorithm that reconstructs the view data 200 into image data 212 having an isotropic voxel size of two millimeters in each spatial dimension. The image data 212 is then communicated to the short-term storage 90 (FIG. 2) and also to the CAD subsystem 100', specifically the AED stage 108. At Step 515, the AED stage 108 performs a preliminary analysis of the image data 212 to ascertain whether the image data 212 contains any area of interest. Any data representing such area of interest image data 101 (FIG. 6) is communicated to the short-term storage 114 (FIG. 2) and to the reconstruction stage 86.

A more rigorous reconstruction and analysis of the area of interest image data 101 is then performed at Step 520 (FIG. 7). Specifically, the reconstruction stage 86 utilizes an algorithm that is intended to enhance the clarity of the area of interest image data 101 by reconstructing the area of interest image data 101 into reconstructed area of interest image data 103. For example, the reconstruction stage 86 may utilize an algorithm that prepares the reconstructed area of interest image data 103 with an isotropic voxel size of one millimeter or less in each spatial dimension. Alternatively, the reconstruction stage 86 may utilize an algorithm that lessens artifacts in the reconstructed area of interest image data 103. The reconstructed area of interest image data 103 is then communicated to the short-term storage 90 and to the AED stage 110. The AED stage 110 analyzes the reconstructed area of interest image data 103 and prepares reanalyzed area of interest image data 105, which is communicated to the short-term storage 114 and to the reconstruction stage 88. The reconstruction stage 88 utilizes yet another algorithm intended to glean even more explicit information from the reanalyzed area of interest image data 105 to ascertain the object within the luggage 22n. The reconstruction stage 88 may utilize an algorithm adapted to vary the voxel size in the reanalyzed area of interest image data 105, or an algorithm adapted to compensate for noise in the reanalyzed area of interest image data 105, or an algorithm adapted to iteratively and statistically reconstruct the acquired information into the image data, or any other suitable algorithm. This re-reconstructed area of interest image data 107 is communicated to the short-term storage 90 and to the AED stage 112 for a final analysis.

At any point in the analysis performed by the CAD subsystem 100', the risk variables 21 may be utilized to alter the parameters of the analysis. Alternatively, the risk variables 21 may be utilized to alter the parameters of the analysis at AED stages 108, 110, 112 of the process. Similarly, information from other sources, i.e., a trace detection subsystem or a multiple-energy-discriminating scan, may be communicated to the CAD subsystem 100' to alter its analysis parameters.

In an alternative process, the acquisition subsystem 30 may communicate the intensity measurements directly to the AED stage 108 of the CAD subsystem 100'. The AED stage 108 then processes these measurements to generate view data 200 and analyzes the view data 200 to ascertain an area of interest therein. Although not illustrated, and the AED stage 108 may then communicate that area of interest view data to the reconstruction stage 84. The reconstruction stage 84 then reconstructs the area of interest view data into area of interest image data. The remainder of this alternative process follows the process steps described above with regard to FIGS. 6 and 7.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. For example, although the exemplary embodiments have been described in reference to the scanning of luggage to detect explosives, it should be appreciated that the invention may be used for other purposes, such as, for example, detecting cancerous growths within a human body. Also, while the illustrated embodiments of the invention have described two or three reconstruction stages and three AED stages, it should be appreciated that more or less such stages may be employed. Furthermore, although the illustrated acquisition subsystems have been shown as having a CT scanner with detectors positioned in a circular pattern, it should be appreciated that planar arrays of detectors or any other configuration of detectors may be utilized provided they are capable of obtaining an appropriate set of view data for the subject article being scanned. Also, although CT scanners have been illustrated as exemplary components of acquisition subsystems, it should be appreciated that a suitable x-ray based system, such as, for example, digital radiography, may be employed. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A system for detecting an explosive within an article, comprising:

an energy-discriminating acquisition subsystem including an x-ray computed tomography scanner having a stationary radiation source and a stationary detector, said acquisition subsystem is adapted to acquire intensity measurements pertaining to the explosive;

a means for conveying articles to be scanned through the computed tomography scanner; and a reconstruction subsystem, in communication with the acquisition subsystem, for generating view data from the intensity measurements and for reconstructing the view data into image data representative of the explosive, wherein said reconstruction subsystem utilizes three-dimensional reconstruction techniques;

wherein the acquisition subsystem acquires image data of the articles for three-dimensional reconstruction without rotating the articles.

2. The system of claim 1, wherein the computed tomography scanner comprises:
a vacuum housing chamber for generating an electron beam;
a target for receiving the electron beam and emitting x-rays in response to the electron beam; and
a detector array located opposite the target for receiving the emitted x-rays.

3. The system of claim 1, wherein the computed tomography scanner comprises:
a source ring including a plurality of stationary x-ray sources; and
a detector ring adjacent to the source ring and including a plurality of discrete detector modules.

4. The system of claim 1, wherein the reconstruction subsystem comprises a plurality of reconstruction stages.

5. The system of claim 4, wherein the plurality of reconstruction stages comprises one reconstruction stage including an algorithm adapted to reduce artifacts in the image data.

6. The system of claim 4, wherein the plurality of reconstruction stages comprises one reconstruction stage including an algorithm adapted to vary the voxel size in the image data.

7. The system of claim 4, wherein the plurality of reconstruction stages comprises one reconstruction stage including an algorithm adapted to compensate for noise in the acquired information.

8. The system of claim 4, wherein the plurality of reconstruction stages comprises one reconstruction stage including an algorithm adapted to iteratively and statistically reconstruct the image data.

9. The system of claim 4, further comprising a computer-aided detection subsystem for analyzing the image data.

10. The system of claim 9, wherein the computer-aided detection subsystem comprises a plurality of computer-aided detection stages.

11. The system of claim 10, wherein at least one of the plurality of computer-aided detection stages is in communication with any of the plurality of reconstruction stages.

12. The system of claim 11, wherein at least one computer-aided detection stage is adapted to receive the image data from one of the reconstruction stages, analyze the image data, and identify an area of interest within the image data.

13. The system of claim 12, wherein the computer-aided detection subsystem is adapted to feedback image data of the area of interest to the reconstruction subsystem.

14. The system of claim 1, wherein the acquisition subsystem comprises an energy discriminating detector adapted to acquire energy sensitive measurements.

15. The system of claim 14, wherein the energy discriminating detector includes an assembly of two or more x-ray attenuating materials the signals from which can be processed in either a photon counting or a charge integration mode.

16. The system of claim 1, wherein the acquisition subsystem comprises at least one detector for detecting x-rays from at least two different incident x-ray energy spectra.

17. The system of claim 1, further comprising an alternative modality subsystem.

18. The system of claim 17, wherein the alternative modality subsystem comprises one or more of the group consisting of a coherent scattering subsystem, a quadrupole subsystem, and a trace detection subsystem.

19. The system of claim 1, further comprising a conveyor belt for transporting the article to the acquisition subsystem.

20. A system for detecting an explosive within an article, comprising:
a transportation means for transporting the article without rotating the article;
an energy-discriminating acquisition subsystem comprising an x-ray computed tomography scanning device having a stationary radiation source and a stationary detector and being adapted to acquire intensity measurements from which view data may be derived;
a means for conveying articles to be scanned through the computed tomography scanner;
a reconstruction subsystem, comprising a plurality of reconstruction stages, for reconstructing the view data into image data representative of the explosive, wherein said reconstruction subsystem utilizes three-dimensional reconstruction techniques; and
a computer-aided detection subsystem, comprising a plurality of computer-aided detection stages, for analyzing the image data.

21. The system of claim 20, wherein the computed tomography scanning device comprises:
a vacuum housing chamber for generating an electron beam;
a target for receiving the electron beam and emitting x-rays in response to the electron beam; and
a detector array located opposite the target for receiving the emitted x-rays.

22. The system of claim 20, wherein the computed tomography scanning device comprises:
a source ring including a plurality of stationary x-ray sources; and
a detector ring adjacent to the source ring and including a plurality of discrete detector modules.

23. The system of claim 20, wherein the acquisition subsystem is adapted to communicate the view data to the reconstruction subsystem.

24. The system of claim 23, wherein the reconstruction subsystem is adapted to reconstruct the view data into the image data and communicate the image data to the computer-aided detection subsystem.

25. The system of claim 24, wherein the computer-aided detection subsystem is adapted to identify an area of interest within the image data and direct the reconstruction subsystem to reconstruct the image data for the area of interest.

26. The system of claim 20, wherein the acquisition subsystem is adapted to communicate the view data to the computer-aided detection subsystem.

27. The system of claim 26, wherein the computer-aided detection subsystem is adapted to identify an area of interest within the view data and direct the reconstruction subsystem to reconstruct the view data into image data for the area of interest.

28. The system of claim 20, wherein the plurality of reconstruction stages comprises one reconstruction stage including an algorithm adapted to reduce artifacts in the acquired information.

29. The system of claim 20, wherein the plurality of reconstruction stages comprises one reconstruction stage including an algorithm adapted to vary the voxel size in the image data.

30. The system of claim 20, wherein the plurality of reconstruction stages comprises one reconstruction stage including an algorithm adapted to compensate for noise in the acquired information.

31. The system of claim 20, wherein the plurality of reconstruction stages comprises one reconstruction stage including an algorithm adapted to iteratively and statistically reconstruct the acquired information into the image data.

32. The system of claim 20, wherein at least one of the plurality of computer-aided detection stages is in communication with any of the plurality of reconstruction stages.

33. The system of claim 20, wherein the acquisition subsystem comprises an energy discriminating detector adapted to acquire energy sensitive measurements.

34. The system of claim 33, wherein the energy discriminating detector includes an assembly of two or more x-ray attenuating materials the signals from which can be processed in either a photon counting or a charge integration mode.

35. The system of claim 20, wherein the acquisition subsystem comprises at least one detector for detecting x-rays from at least two different incident x-ray energy spectra.

36. The system of claim 20, further comprising an alternative modality subsystem.

37. The system of claim 36, wherein the alternative modality subsystem comprises one or more from the group consisting of a coherent scattering subsystem a quadrupole subsystem, and a trace detection subsystem.

38. The system of claim 20, wherein the transportation means comprises a conveyor belt.

39. A system for detecting an explosive within an article, comprising:
an energy-discriminating acquisition subsystem including an x-ray computed tomography scanner having a stationary radiation source for acquiring intensity measurements pertaining to the explosive;
a means for conveying articles to be scanned through the computed tomography scanner;
a reconstruction subsystem, in communication with the acquisition subsystem, for generating view data from the intensity measurements and for reconstructing the view data into image data, wherein said reconstruction subsystem utilizes three-dimensional reconstruction techniques;
a computer-aided detection subsystem for analyzing the image data; and
at least one additional source of information pertaining to the explosive, wherein the image data and the at least one additional source of information assist in identifying the explosive,
wherein the acquisition subsystem acquires image data of the article for three-dimensional construction without rotating the articles.

40. The system of claim 39, wherein the at least one additional source of information comprises an energy discriminating detector for discriminating between high and low energy signatures.

41. The system of claim 40, wherein the energy discriminating detector comprises a high-energy sensitive detector and a low energy sensitive detector.

42. The system of claim 40, wherein the energy discriminating detector comprises at least one detector for detecting x-rays from at least two different incident x-ray energy spectra.

43. The system of claim 39, wherein the at least one additional source of information comprises an alternative modality subsystem.

44. The system of claim 43, wherein the alternative modality subsystem comprises one or more from the group consisting of a coherent scattering subsystem, a quadrupole subsystem, and a chemical trace detection subsystem.

45. The system of claim 39, wherein the at least one additional source of information comprises a risk variable subsystem.

46. A method for detecting an explosive within an article, comprising:
acquiring information pertaining to the explosive with an energy-discriminating acquisition apparatus having an x-ray computed tomography scanner with a stationary radiation source and a stationary detector;
a means for conveying articles to be scanned through the computed tomography scanner; and
reconstructing an image representative of the explosive based upon the acquired information, wherein said reconstructing includes reconstructing the acquired information into a three-dimensional image;
wherein the acquisition subsystem acquires image data of the articles for three-dimensional reconstruction without rotating the articles.

47. The method of claim 46, wherein the acquiring of information step is accomplished with the computed tomography scanner comprising:
a vacuum housing chamber for generating an electron beam;
a target for receiving the electron beam and emitting x-rays in response to the electron beam; and
a detector array located opposite the target for receiving the emitted x-rays.

48. The method of claim 46, wherein the acquiring of information step is accomplished with the computed tomography scanner comprising:
a source ring including a plurality of stationary x-ray sources; and
a detector ring adjacent to the source ring and including a plurality of discrete detector modules.

49. The method of claim 46, further comprising transporting the article to a location for the acquiring information step.

50. The method of claim 46, wherein the reconstructing an image step comprises subjecting the acquired information to at least one reconstruction technique to form image data representative of the explosive.

51. The method of claim 50, wherein the reconstructing an image step comprises subjecting the acquired information to at least one technique in the group consisting of an algorithm adapted to reduce artifacts in the acquired information, an algorithm adapted to vary the voxel size in the image data, an algorithm adapted to compensate for noise in the acquired information, and an algorithm adapted to iteratively and statistically reconstruct the acquired information into the image.

52. The method of claim 46, further comprising analyzing the reconstructed image to identify the explosive.

53. The method of claim 52, further comprising recomputing area of interest image data.

54. The method of claim 46, further comprising obtaining additional information through an alternative modality subsystem.

55. The method of claim 54, wherein the alternative modality subsystem comprises one or more from the group consisting of a coherent scattering subsystem, a quadrupole subsystem, and a chemical trace detection subsystem.

56. A method for detecting an explosive within an article, comprising:
acquiring information pertaining to an object located within the article with an energy-discriminating x-ray computed tomography machine having a stationary radiation source and a stationary detector;
a means for conveying articles to be scanned through the computed tomography scanner;
communicating the acquired information to a plurality of reconstruction modules;

reconstructing the acquired information into image data with the plurality of reconstruction modules, wherein said reconstructing includes reconstructing the acquired information into a three-dimensional image; and analyzing the image data to identify whether the object is an explosive device;

wherein the acquisition subsystem acquires image data of the articles for three-dimensional reconstruction without rotating the articles.

57. The method of claim 56, wherein the acquiring information step comprises acquiring information with the computed tomography machine comprising:
   a vacuum housing chamber for generating an electron beam;
   a target for receiving the electron beam and emitting x-rays in response to the electron beam; and
   a detector array located opposite the target for receiving the emitted x-rays.

58. The method of claim 56, wherein the acquiring information step is accomplished with the computed tomography machine comprising:
   a source ring including a plurality of stationary x-ray sources; and
   a detector ring adjacent to the source ring and including a plurality of discrete detector modules.

59. The method of claim 56, wherein the reconstructing the acquired information step comprises reducing artifacts in the image data.

60. The method of claim 56, wherein the reconstructing the acquired information step comprises varying the voxel size in the image data.

61. The method of claim 56, wherein the reconstructing the acquired information comprises compensating for noise in the image data.

62. The method of claim 56, wherein the reconstructing the acquired information comprises iteratively and statistically reconstructing the acquired information into the image.

63. The method of claim 56, further comprising obtaining additional information through an alternative modality subsystem.

64. The method of claim 63, wherein the alternative modality subsystem comprises one or more from the group consisting of a coherent scattering subsystem, a quadrupole subsystem, and a chemical trace detection subsystem.

65. The method of claim 56, further comprising transporting the article to the scanning device with a conveyor belt.

66. A method for detecting an object, comprising:
   scanning an article with an energy-discriminating x-ray computed tomography machine to acquire information pertaining to the object, wherein the computed tomography machine includes a stationary radiation source and a stationary detector;
   a means for conveying articles to be scanned through the computed tomography scanner;
   discriminating between high-energy and low-energy signatures;
   reconstructing image data representative of the object based upon the high-energy and low-energy signatures, wherein said reconstructing includes reconstructing the information derived from the high-energy and low-energy signatures into a three-dimensional image; and
   analyzing the reconstructed image to identify the object;
   wherein the acquisition subsystem acquires image data of the articles for three-reconstruction without rotating the article.

67. The method of claim 66, wherein the discriminating step comprises distinguishing between absorption coefficients originating from photoelectric and Compton scatter processes.

68. The method of claim 67, wherein the discriminating step is accomplished with an energy discriminating detector comprising an energy sensitive detector.

69. The method of claim 68, wherein the discriminating step is accomplished with an energy discriminating detector comprising at least one detector adapted to perform measurements by at least two distinctive incident x-ray energy spectra.

70. The method of claim 68, wherein the article is a human body and the object is within the human body.

* * * * *

UNITED STATES PATENT AND TRADEMARK OFFICE
CERTIFICATE OF CORRECTION

PATENT NO. : 7,492,855 B2
APPLICATION NO. : 10/743195
DATED : February 17, 2009
INVENTOR(S) : Hopkins et al.

It is certified that error appears in the above-identified patent and that said Letters Patent is hereby corrected as shown below:

In Column 14, Line 46, in Claim 51, delete "image." and insert -- image data. --, therefor.

In Column 15, Line 37, in Claim 62, delete "image." and insert -- image data. --, therefor.

Signed and Sealed this

First Day of September, 2009

David J. Kappos
*Director of the United States Patent and Trademark Office*